(12) United States Patent
Dinh et al.

(10) Patent No.: US 8,580,994 B2
(45) Date of Patent: Nov. 12, 2013

(54) PROCESS FOR THE PREPARATION OF HALOALKYLALKOXYSILANES AND HALOALKYLHALOSILANES

(75) Inventors: Paul Charles Dinh, Midland, MI (US); Keiji Wakita, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 341 days.

(21) Appl. No.: 12/867,337

(22) PCT Filed: Jan. 13, 2009

(86) PCT No.: PCT/US2009/030793
§ 371 (c)(1),
(2), (4) Date: Aug. 12, 2010

(87) PCT Pub. No.: WO2009/111095
PCT Pub. Date: Sep. 11, 2009

(65) Prior Publication Data
US 2010/0317885 A1    Dec. 16, 2010

Related U.S. Application Data

(60) Provisional application No. 61/034,191, filed on Mar. 6, 2008.

(51) Int. Cl.
C07F 7/14 (2006.01)

(52) U.S. Cl.
USPC .......................................... 556/479; 556/414

(58) Field of Classification Search
None
See application file for complete search history.

(56) References Cited

U.S. PATENT DOCUMENTS

| 3,159,601 A | 12/1964 | Ashby |
| 3,178,464 A | 4/1965 | Pierpoint |
| 3,188,299 A | 6/1965 | Chalk |
| 3,220,972 A | 11/1965 | Lamoreaux |
| 3,296,291 A | 1/1967 | Chalk |
| 3,419,593 A | 12/1968 | Willing |
| 3,474,123 A | 10/1969 | Kelly et al. |
| 3,516,946 A | 6/1970 | Modic |
| 3,564,266 A | 2/1971 | Klotz, Jr. |
| 3,715,334 A | 2/1973 | Karstedt |
| 3,814,730 A | 6/1974 | Karstedt |
| 4,658,050 A | 4/1987 | Quirk et al. |
| 5,616,762 A | 4/1997 | Kropfgans et al. |
| 6,359,161 B2 | 3/2002 | Tonomura et al. |
| 6,388,119 B1 | 5/2002 | Bauer et al. |
| 2005/0240043 A1 | 10/2005 | Kornek et al. |
| 2006/0167296 A1 | 7/2006 | Guennouni et al. |
| 2009/0036702 A1* | 2/2009 | Baumann et al. ............ 556/476 |

FOREIGN PATENT DOCUMENTS

| DE | 1165028 | 3/1964 |
| EP | 0602922 | 8/1984 |
| EP | 1481978 | 12/2001 |
| GB | 2019426 | 10/1979 |
| JP | 2768159 | 4/1998 |
| JP | 2938731 | 6/1999 |
| WO | WO03048169 | 6/2003 |
| WO | WO2004009607 | 1/2004 |
| WO | WO2004016628 | 2/2004 |
| WO | WO2004113354 | 12/2004 |
| WO | WO2006045533 | 5/2006 |

OTHER PUBLICATIONS

Saiki et al Organometallics, 2006, 25, 6068-6073.*
Tanaka et al., Ruthenium complex-catalyzed hydrosilylation of allyl chloride with trimethoxysilane, Journal of Molecular Catalysis, 81 (1983) 207-214.
Gustafsson et al., The effect of oxygen on the regioselectivity in the rhodium catalysed hydrosilylation of 1,3-dienes, J. Chem. Soc., Perkin Trans. 1, 2002, 102-107.

* cited by examiner

*Primary Examiner* — Yevegeny Valenrod
(74) *Attorney, Agent, or Firm* — Matthew T. Fewkes

(57) ABSTRACT

This invention involves a process for the preparation of haloalkylalkoxysilanes and haloalkylhalosilancs. The process comprises reacting an alkoxyhydridosilane or a halohydridosilanc silane with an alkenylhalide compound in the presence of a catalytic amount of an iridium containing catalyst. When a halohydridosilane is the silane reactant. The resulting haloalkylhalosilane may be alkoxylated by reaction with a $C_1$-$C_6$ alcohol. In another aspect of the invention, the reacting is conducted under a reduced oxygen atmosphere to improve the catalyst activity and the yield of the resulting haloalkylhalosilane or haloalkylalkox vsi lane.

13 Claims, No Drawings

PROCESS FOR THE PREPARATION OF HALOALKYLALKOXYSILANES AND HALOALKYLHALOSILANES

CROSS-REFERENCE TO RELATED APPLICATIONS

This application is a U.S. national stage filing under 35 U.S.C. §371 of PCT Application No. PCT/US09/30793 filed on Jan. 13, 2009, currently pending, which claims the benefit of U.S. Provisional Patent Application No. 61/034,191 filed Mar. 6, 2008, under 35 U.S.C. §119 (e). PCT Application No. PCT/US09/30793 and U.S. Provisional Patent Application No. 61/034,191 are hereby incorporated by reference.

BACKGROUND OF THE INVENTION

Alkoxysulfidosilane compounds are used in the manufacture of tires as coupling agents, The alkoxysulfidosilane compounds couple fillers into the rubber, reducing the amount of filler required in the tire formulation and improving the performance of the resulting rubber. This invention pertains to the process of manufacturing haloalkylalkoxysilanes, which are key intermediates in the production of alkoxysulfidosilanes.

The production of haloalkylalkoxysilanes is documented in the literature. One means of producing a haloalkylalkoxysilane is through the hydrosilation of an alkenylchloride compound, such as allyl chloride, in the presence a catalyst. Some catalysts that can promote these hydrosilation reactions comprise compounds containing platinum, rhodium, or iridium, For instance, platinum containing hydrosilation catalysts and their use are disclosed in U.S. Pat. Nos. 2,823,218, 3,814,730, 3,715,334, 3,516,946, 3,474,123, 3,419,593, 3,220,972, 3,188,299, 3,178,464, 3,159,601, German Patent No. 1,165,028 and published U.K. Patent Application No. 2,019,426A. Hydrosilation over chloro-rhodium compounds is disclosed in U.S. Pat. Nos. 3,296,291 and 3,564,266; and, hydrosilation over iridium compounds has been disclosed in U.S. Pat. No. 4,658,050, U.S. Pat. No. 6,359,161, U.S. Pat. No. 6,388,119 US 2006/0167296, U.S. Pat. No. 5,616,762, US 2005/0240043, JP2768159, JP2938731 WO 2004/113354, and WO 2003048169.

The present inventors have found that certain iridium compounds, when used according to the process of the invention, generate haloalkylhalosilanes and haloalkylalkoxysilanes in good yields. The present inventors have also found that, in contrast to platinic catalysts, by restricting the exposure of iridium catalysts to oxygen, the activity of the catalyst can be improved and/or prolonged.

BRIEF SUMMARY OF THE INVENTION

This invention involves a novel process for the preparation of a compound of formula (I):

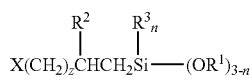

(I)

wherein each $R^1$ and each $R^3$ independently are alkyl groups having from 1 to 6 carbon atoms; $R^2$ is $R^1$ or hydrogen; X is chloro, fluoro, bromo or iodo; n has a value of 0, 1, or 2; z is an integer from 1 to 5. The process comprises reacting a silane of formula (II) or (VI)

(II)

or

(VI)

wherein each $R^1$, $R^3$, X, and n are as defined above, with an alkenylhalide compound having the formula (III):

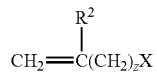

(III)

wherein $R^2$, X, and z are as defined above, in the presence of a catalytic amount of an iridium containing catalyst of formula (IV) or (V)

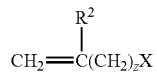

(IV)

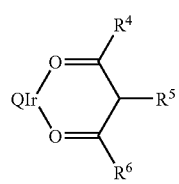

(V)

wherein Q independently is selected from 1,3-butadiene, 1,3-hexadiene, 1,3-cyclohexadiene, 1,3-cyclooctadiene, 1,5-cyclooctadiene and norbornadiene, L is $C_1$-$C_6$ alkoxy; $R^4$ is independently hydrocarbyl, halohydrocabyl, cyanoalkyl, alkoxy, cyanoalkoxy, amino, or hydrocarbyl-substituted amino; $R^5$ is independently hydrogen, hydrocarbyl, halohydrocarbyl, or acyl; and $R^6$ is independently hydrocarbyl, halohydrocarbyl, or cyanoalkyl.

When a silane of formula (VI) is the silane reactant, the reaction between the silane and the alkenylhalide (III) may be subsequently followed by alkoxylation of the product by reaction with a $C_1$-$C_6$ alcohol to form the alkoxy functionality of the haloalkylalkoxysilane of formula (I). In another aspect of the invention, the reaction between the silane (II) or (VI) and the alkenylhalide (III) in the presence of catalyst (IV) or (V) is conducted under a reduced oxygen content atmosphere to improve the iridium catalyst activity and the yield of the resulting haloalkylhalosilane or haloalkylalkoxysilane compound.

DETAILED DESCRIPTION OF THE INVENTION

This invention involves a novel process for the preparation of a compound of formula (I):

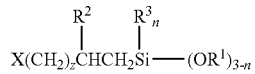

(I)

wherein each $R^1$ and each $R^3$ independently are alkyl groups having from 1 to 6 carbon atoms; $R^2$ is hydrogen, or an alkyl group having from 1 to 6 carbon atoms; X is chloro, fluoro, bromo or iodo; n has a value of 0, 1, or 2; z is an integer from 1 to 5; and wherein the process comprises reacting a silane of formula (II) or (VI)

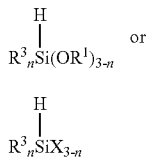

Wherein each $R^1$, $R^3$, X, and n are as defined above, with an alkenylhalide compound of formula (III):

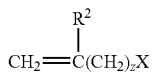

wherein $R^2$, X. and z are as defined above, in the presence of a catalytic amount of an iridium containing catalyst of the formula selected from formula (IV) and (V)

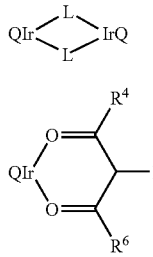

wherein Q is selected from 1,3-butadiene, 1,3-hexadiene, 1,3-cyclohexadiene, 1,3-cyclooctadiene, 1,5-cyclooctadiene and norbornadiene; L is a $C_1$-$C_6$ alkoxy group; $R^4$ is independently hydrocarbyl, halohydrocabyl, cyanoalkyl, alkoxy, cyanoalkoxy, amino, or hydrocarbyl-substituted amino; $R^5$ is independently hydrogen, hydrocarbyl, halohydrocarbyl, or acyl; and $R^6$ is independently hydrocarbyl, halohydrocarbyl, or cyanoalkyl. When a silane of formula (VI) is the halosilane reactant, the reaction may be subsequently followed by treatment with a $C_1$-$C_6$ alcohol to form the alkoxy functionality of the haloalkylalkoxysilane (I). In another aspect of the invention, the reaction atmosphere is reduced in oxygen content and the reaction is conducted under a reduced oxygen atmosphere to improve the activity of the catalyst and the yield of the target compound of formula (I) or (IX).

As indicated above, the process of the invention is conducted by causing an alkenylhalide of formula (III) to react with a silane of formula (II) or (VI) in the presence of an iridium catalyst according to formula (IV) or (V). If the silane in the process is according to formula (VI), then an intermediate of formula (IX) is formed:

wherein $R^2$, $R^3$, z, and n are as defined above and each X is independently chloro, bromo, fluoro, or iodo.

In the case when intermediate (IX) is formed, the process of the invention may further comprise the alkoxylation of intermediate (IX) by treatment with a $C_1$ to $C_6$ alcohol of formula (X) to produce a haloalkylalkoxysilane compound of formula (I).

(X)$R^1$OH.

wherein $R^1$ is as defined above. In one embodiment, $R^1$ is methyl, and, in another embodiment, $R^1$ is ethyl.

Silanes useful in the instant process are those of the formula (I and (VI)

wherein each $R^1$ and $R^3$ independently are alkyl groups having from 1 to 6 carbon atoms, X is chloro, fluoro, bromo or iodo, and n has a value of 0, 1 or 2. In one embodiment, silane materials useful in the process include those wherein n is 1 and $R^1$ and $R^3$ are independently methyl, ethyl, propyl, isopropyl or butyl groups; in another embodiment, the silane materials useful in the process include those wherein n is 2 and $R^1$ and $R^3$ are independently methyl, ethyl, propyl, isopropyl or butyl groups. In yet another embodiment, silane materials useful in the process include those according to formulas (II) and (VI) above wherein n is 0 and $R^1$ is methyl, ethyl, propyl, isopropyl or butyl. Illustrative of the silanes useful in the process of this invention are triethoxysilane, trimethoxysilane, tripropoxysilane, tri-isopropoxysilane, tributoxysilane, methyldimethoxysilane, ethyldimethoxysilane, methyldiethoxysilane, dimethylmethoxysilane, dimethylethoxysilane, dimethylpropoxysilane, dimethylbutox trichlorosilane, monomethyldichlorosilane, and dimethylmonochlorosilane. Silanes useful in the present invention can either be bought commercially or made by one with skill in the art. One with skill in the art would know how to prepare the silanes useful in the present invention.

Alkenylhalides useful in the process of this invention are those of formula III):

wherein $R^2$ is hydrogen or a $C_1$-$C_6$ alkyl group, X is chloro, bromo, fluoro, or iodo, and z is an integer from 1 to 5. Examples of useful alkenylhalide compounds are allyl halides. Examples of allyl halides useful in the present invention include allyl chloride, methallyl chloride, allyl bromide, methallyl bromide, allyl iodide, and methallyl iodide. In one embodiment, the alkenylhalide is allyl chloride in another embodiment the alkenylhalide is methallyl chloride. The alkenylhalides useful in the invention are available commercially.

The weight ratio of the silane starting material to alkenylhalides useful in the process of this invention can vary. One skilled in the art would know how to vary the ratio of silane to alkenylhalide to achieve the best yields. In one embodiment, the silane and alkenylhalide are in a ratio of from 5:1 to 1:5; in another embodiment, the ratio of silane to alkenylhalide is from 1.5:1 to 1:1.5; in yet another embodiment, in the ratio is about 1:1, In some embodiments, it may be desirable to use, instead of an exact 1:1 ratio, a slight excess, e.g., 10 mole %, of either the silane or the alkenylhalide to ensure complete reaction of the other reactant. Therefore, in one embodiment the silane and the alkenylhalide are in a near 1:1 ratio with a slight excess of one of the reactants over the other. One skilled in the art would know how to adjust the quantities of the reactants to ensure an excess to completely consume one of the reactants.

The iridium catalysts useful in the process of the claimed invention comprise iridium compounds selected from those compounds according to formula (IV)

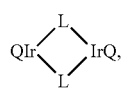
(IV)

wherein Q is selected from 1,3-butadiene, 1,3-hexadiene, 1,3-cyclohexadiene, 1,3-cyclooctadiene, 1,5-cyclooctadiene and norbornadiene and L is an alkoxy group containing to 6 carbon atoms, and those of formula (V)

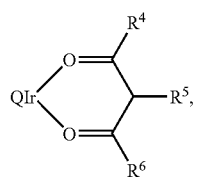
(V)

wherein Q is as defined above and $R^4$ is independently hydrocarbyl, halohydrocabyl, cyanoalkyl, alkoxy, cyanoalkoxy, amino, or hydrocarbyl-substituted amino; $R^5$ is independently hydrogen, hydrocarbyl, halohydrocarbyl, or acyl; and $R^6$ is independently hydrocarbyl, halohydrocarbyl, or cyanoalkyl. In one embodiment, the catalyst of the invention is a complex of iridium, 1,5-cyclooctadiene, and acetylacetonate of representative structure (VII) below. One skilled in the art will recognize that the complex (IV) may also be represented by its keto-enol tautorner. In another embodiment, the iridium catalyst is the iridium dimer complex [Ir(OCH$_3$)(1,5-cyclooctadiene)]$^2$ of representative structure (VIII) below.

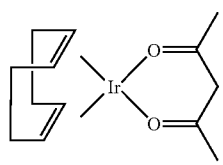
(VII)

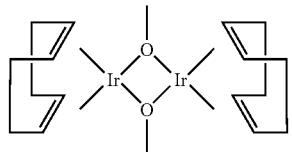
(VIII)

The preparation of the catalysts used in the process of this invention is well documented in the literature. The catalysts according to representative formulations (VII) and (VIII) may be obtained commercially. Alternatively, catalytic complexes other than those that contain 1,5-cycloctadiene (COD) may also be purchased commercially or be prepared by displacement reaction with an [Ir(COD)Cl]$_2$, [Ir(COD)2]BF$_4^-$, H$_2$IrChl$_6$, IrCl$_3$, or [Ir(1,5-cyclooctadiene)]$_2$ material, and an excess of the desired diene. The catalyst so-produced may then be recovered as a solid.

The concentration of the iridium-containing catalyst complexes used in the process may vary. In general the iridium-containing catalyst complexes should be used in a catalytic effective amount. One skilled in the art would know how to add the iridium catalysts and how to determine a catalytic effective amount to use in the reaction. There is really no upper limit to the amount of iridium catalyst that may be used according to the invention; however, constraints such catalyst solubility and economic considerations will put practical limits on the amount of catalyst used. The minimum amount of iridium catalyst required for the reaction will depend upon reaction temperature and reaction time. In general, the iridium catalyst should be present in the process at a level such that iridium (as opposed to the iridium catalyst) is present in the process at ≥5 mole ppm iridium. In one embodiment, the catalyst is present at ≥40 mole ppm iridium; in another embodiment, from 5-900 mole ppm iridium; in another embodiment, from 10-900 mole ppm iridium; in another embodiment, from 10-250 mole ppm iridium; in another embodiment, from 10-100 mole ppm iridium; and, in yet another embodiment, from 50-100 mole ppm iridium. As used herein, "mole ppm iridium" or "mole ppm catalyst" always refers to moles of elemental iridium (as opposed to catalyst) per million moles of the reactant that is present in the least amount (i.e., the limiting reactant).

The catalyst is not consumed in the reaction and, therefore, may be recycled. One skilled in the art would know how to recycle the catalyst. For example, the reaction products may be separated by distillation, and the catalyst could be recycled by applying additional loads of reagents to the distillation residue containing the catalyst. Additional catalyst may be added to the reaction with the recycled catalyst as a supplement to the recycled catalyst. Recycling of the catalyst may be improved by adding an additional amount of the catalyst ligand and/or by putting the recycled catalyst in contact with an adsorbing agent such as carbon black, activated charcoals, molecular sieves, which may be synthetic zeolites, silicates, or metal aluminosilicates, silicas, activated aluminas, diatomite- and perlite-based adsorbent, activated and ground clays based on bentonite, ion-exchange resins, or amberlite or amberlyst resin.

The temperature at which the hydrosilation reaction can be conducted may vary. Once skilled in the art would know how to vary the temperature of the reaction to achieve the best yields. In one embodiment, the hydrosilation reaction of the process is conducted at a temperature from 20° C. to 200° C.; in another embodiment, from 30° C. to 150°; in another embodiment, from 30° C. to 125° C.; in another embodiment from 30° C. to 85° C.; in another embodiment, from 30° C. to 80"C'; in another embodiment, from 30° C. to 60° C.; in another embodiment from 40° C. to 60° C.; in another embodiment from 60° C. to 125° C.

The pressure at which the reaction is conducted may vary. One skilled in the on would know how to vary the reaction pressure conditions. The pressure of the reaction is not critical and can vary from atmospheric to super-atmospheric pressure. In one embodiment, the process is carried out at atmospheric pressure conditions; in another embodiment, the pressure is above atmospheric conditions; in another embodiment from atmospheric pressure to 500 psig.

The oxygen content of the reaction atmosphere will affect the reaction yields and the activity of iridium catalysts. Generally, the lower the oxygen content of the reaction atmosphere the better the yield and the longer the iridium catalyst activity. This result is unexpected because the result is the opposite for platinum containing catalysts in hydrosilation reactions, Platinic catalysts have longer and better activity when oxygen is in the reactants and/or hydrosilation reaction atmosphere. Therefore, according to the invention, iridium catalyst activity is increased and lengthened by reducing the oxygen content of the reaction atmosphere. In one embodiment, there is less than 5% (v/v) oxygen in the reaction atmosphere; in another embodiment, less than 3% (v/v) oxygen; in another embodiment, less than 2% (v/v) oxygen; and in another embodiment, less than 1% (v/v) oxygen. One skilled in the art would know how to test a reaction atmosphere for the % oxygen through the use of, for example, oxygen gas sensors which are available commercially. The increase in iridium catalyst activity is most apparent at low catalyst concentrations. When larger catalyst concentrations are employed, the effects of the reduced oxygen atmosphere may be obscured.

The oxygen content may be reduced in the reaction atmosphere by standard methods known to those skilled in the art. In one embodiment, oxygen is reduced in the reaction atmosphere by bubbling nitrogen, or some other inert gas, through the reactants prior to their being brought into contact in the reactor and by bubbling nitrogen, or some other inert gas, through the reactants in the reactor during the course of the reaction. Another means of reducing the oxygen content of the reaction atmosphere is by flushing or purging the reactor with nitrogen, or another inert gas, one or more times prior to introducing the reactants into the reactor. In one embodiment of the invention, oxygen is reduced from reaction atmosphere during the course of the react on by bubbling nitrogen through the reactants. In another embodiment, the reactor is purged with nitrogen, or some other inert gas, prior to introducing the reactants. One skilled in the art would know how to purge a reactor prior to introducing reactants into a reactor. When the reaction is conducted under the atmosphere of an inert gas like nitrogen, there reaction may be conducted under a pressure from 0 psig up to 500 psig. One skilled in the art would know how to adjust the pressure to conduct a hydrosilation reaction under an atmosphere of an inert gas.

The reaction time according to the process of this invention may vary. One skilled in the art would know how to monitor the reaction process to determine the progress toward completion (maximum yield) by, for example, measuring the quantity of one or more of the reactants by gas chromatography and/or mass spectrometry (GC/MS). The time required will depend upon conditions such as the amount of catalyst used or the reaction temperature. Generally, higher catalyst concentration and the reaction temperature will shorten the time required for the reaction to reach completion. When the catalyst concentration is in the range of 50-900 mole ppm iridium and the reaction temperature is between about 60° C. to about 125° C., a reaction time of about 2-3 hours is generally sufficient to complete the reaction and process of the invention. The yield of the target compound is not significantly affected when longer reaction times are used. That is, yields will plateau after time and will not continue to increase with longer heating and/or agitation.

Solvent is generally not necessary for the hydrosilation reaction according to the process of this invention. However, the use of solvent may be desired to increase catalyst solubility in the reaction mixture. If a solvent is employed, those useful in the claimed process are (hose which do not adversely react or interact with the reactants, catalyst or reaction products. Suitable solvents include xylene, toluene and heptane. One of the reactants may also function as solvent and may be used in stoichiometric excess.

When a silane of formula (VI) is used in the process, an intermediate according to formula (IX) is produced

(IX)

wherein $R^2$, $R^3$, X, z, and n are as defined above. This intermediate (IX) may be caused to react with a $C_1$-$C_6$ alcohol to give the compound of formula (I). Examples of $C_1$-$C_6$ alcohols useful for this are methanol, ethanol, propanol, butanol, pentanol and hexanol, This alcoholysis is carried out according to known methods in the art. Once skilled in the art would know how to carry out an alcoholysis to produce the compound of formula (I) from intermediate (IX).

The process of the invent on can be conducted either continuously or semi-continuously, or in batches. For example, the process of the invention may be carried out in a multi-tube reactor with a block heater and temperature control. At the end of the process, the reaction product may be separated and collected by methods known in the art such as by distillation of the reaction medium. The reaction may be run in a heterogeneous or homogeneous medium. When operating in a heterogeneous medium, the catalyst may be supported on a solid inert base. This mode of operation is conducive to operating in a fixed bed reactor operating continuously, semi-continuously, or in batches with recycling. One skilled in the art would know the equipment to use and bow to conduct a hydrosilation reaction according to the invention.

The haloalkylalkoxysilanes obtained by the process of this invention are useful, for example, as intermediates in the production of organo-functional slime coupling agents. Where the haloalkylalkoxysilanes have a lower alkoxy content than three alkoxy groups p silicon atom, they emit fewer VOC's during rubber manufacture because there are fewer alkoxy groups to hydrolyze to alcohols. The conversion of the products of the instant invention to said coupling agents is well known in the art as shown, for example, in the Chemistry and Technology of Silicones by Walter Nole (Academy Press, 1968) pages 147, 148 and 158. The conversion comprises replacement of the halogen moiety with, for example, hydroxyl, amino or mercapto groups.

EXAMPLES

The following examples are included to demonstrate embodiments of the invention. It should be appreciated by those of skill in the art that the techniques disclosed in the examples which follow represent techniques discovered by the inventor to function well in the practice of the invention, and thus can be considered to constitute modes for its practice. However, those of skill in the art should, in light of the present disclosure, appreciate that many changes can be made in the specific embodiments which are disclosed and still obtain a like or similar result without departing from the spirit and scope of the invention. Unless otherwise noted, all percentages are in wt. %.

Key to Tables:
Ir—iridium
MEK—Methyl ethylketone
COD—1,5-cyclooctadiene
CO—carbon monoxide
Acac—acetylacetonate
ND—None detected
A—$Cl(CH_2)_3Si(CH_3)_2(OCH_2CH_3)$
B—$ClSi(CH_3)_2(OCH_2CH_3)$
C—$CH_3(CH_2)_2Si(CH_3)_2(OCH_2CH_3)$ Dimethylethoxysilane was prepared from dimethylchlorosilane and ethanol by using a continuous alkoxylation column. $[Ir(COD)Cl]_2$ was obtained from Johnson Matthey. All of the other catalysts allyl chloride were purchased from the Strem Chemical or Sigma-Aldrich Companies.

Example 1-6

Iridium catalyst was dissolved in 2 grams allyl chloride or methyl ethylketone, depending upon solubility. Enough of this catalyst solution to give a catalyst concentration of one hundred mole parts per million (ppm) of iridium based upon the 20 millimoles of ally chloride and 20 millimoles of dimethylethoxysilane reactants, was combined with 20 millimoles of allyl chloride reactant and mixed and cooled in dry ice until the mixture reached −78° C. The cooled catalyst and allyl chloride mixture was then mixed with 20 millimoles of similarly cooled dimethylethoxysilane in a 40 milliliter glass tube of a multi-tube batch reactor consisting of 10 pressure tight glass tubes, Teflon caps with O-rings, and a block heater with a temperature controller. The reactant-catalyst mixture was then heated to and then held at 60° C. for one hour. After one hour, the reaction was stopped, or quenched, by cooling with dry ice. The resulting mixture was analyzed by gas chromatography (GC) to determine the area % of each of the major materials present. The results are listed in Table 1.

As can be seen in Table 1, the Ir(acac)(COD) catalyst provided the best selectivity for the desired product $Cl(CH_2)_3SiMe_2(OCH_2CH_3)$ compared to the other iridium catalysts tested at 100 mole ppm iridium.

Examples 7-10

The same procedure and reactant and catalyst amounts used in examples 1-6 were used in examples 7-11 except reactants were heated to and held at 40° C. rather than at 60° C. The results are listed in Table 2.

TABLE 2

Comparison of the catalyst of the invention and comparative catalysts at 40° C. reaction temperature and 100 mole ppm iridium.

| | | | Reaction Products (%) | | |
|---|---|---|---|---|---|
| Example No. | Catalyst | Solvent | A | B | C |
| 7 (comparative) | $[Ir(COD)Cl]_2$ | Allyl Chloride | 82.3 | 3.3 | 2.6 |
| 8 (comparative) | IrCl3 hydrate | MEK | 9.7 | trace | 1.6 |
| 9 | Ir(acac)(COD) | Allyl Chloride | 72.5 | 8.9 | 3.0 |
| 10 (comparative) | $H_2IrCl_6$ hydrate | MEK | 75.1 | 3.5 | 3.9 |

As can be seen in Table 2, example 9, which is according to the invention, produced good yields of the target compound, $Cl(CH_2)_3Si(CH_3)_2(OCH_2(CH_3)$.

Examples 11-14

The same procedure and reactant amounts as were used in examples 1-6 were used in examples 11-14, except that the reactants were heated to and held at 40° C. and that the amount of catalyst was reduced to 25 mole ppm. A more dilute catalyst solution was prepared with 4 grams of catalyst solvent (allyl chloride or MEK) to combine with the reactants and achieve the desired catalyst concentration.

TABLE 1

Comparison of iridium catalysts of the invention with comparative catalysts at 60° C. and 100 mole ppm iridium.

| | Catalyst | | Reaction Products (GC area %) | | |
|---|---|---|---|---|---|
| Example No. | Catalyst | Solvent | A | B | C |
| 1 (comparative) | $[Ir(COD)Cl]_2$ | Allyl Chloride | 65.4 | 14.6 | 3.5 |
| 2 (comparative) | $(Ph_3P)_2IrCl(CO)$ | Allyl Chloride | 17.6 | 9.6 | 4.1 |
| 3 (comparative) | $IrCl_3$ hydrate | MEK | 64.4 | 2.3 | 3.8 |
| 4 | Ir(acac)(COD) | Allyl Chloride | 73.5 | 7.4 | 4.1 |
| 5 (comparative) | $IrClH_2[Pr_2PCH_2CH_2)_2NH]$ | Allyl Chloride | ND | ND | ND |
| 6 (comparative) | $H_2IrCl_6$ hydrate | MEK | 58.2 | 8.7 | 4.5 |

TABLE 3

Comparison of the catalyst of the invention and comparative catalysts at 40° C. reaction temperature and 25 mole ppm catalyst.

| | Catalyst | | Reaction Products (%) | | |
|---|---|---|---|---|---|
| Example No. | Catalyst | Solvent | A | B | C |
| 11 (comparative) | [Ir(COD)Cl]$_2$ | Allyl Chloride | 80.4 | 1.5 | 2.3 |
| 12 | Ir(acac)(COD) | Allyl Chloride | 76.7 | 1.0 | 2.2 |
| 13 (comparative) | H$_2$IrCl$_6$ hydrate | MEK | 6.8 | 0.3 | 1.8 |
| 14 (comparative) | H$_2$IrCl$_6$ hydrate | IPA | 17.1 | trace | 1.7 |

As can be seen in Table 3, at 40"C and 25 mole ppm catalyst concentration, the iridium catalyst in example 12 produces good yields of the target compound, Cl(CH$_2$)$_3$SiMe$_2$(OEt).

Examples 15-16

The same procedure and reactant amounts as were used in examples 1-6 were used in examples 15-16, except that the reactants were heated to and held at 40° C., the amount of catalyst was reduced to 10 mole ppm using the same catalyst solution described for examples 11-14, and the reaction was conducted for 1 and 2 hours,

TABLE 4

Comparison of the catalyst of the invention and comparative catalyst at 40° C. reaction temperature, for one and two hours, and 10 mole ppm iridium.

| | | Time | Reaction Products (%) | | |
|---|---|---|---|---|---|
| Example No. | Catalysts | (hrs.) | A | B | C |
| 15 (comparative) | [Ir(COD)Cl]$_2$ | 1 | 22.6 | Trace | 1.7 |
| | | 2 | 24.0 | 0.3 | 2.6 |
| 16 | Ir(acac)(COD) | 1 | 38.3 | trace | 1.9 |
| | | 2 | 41.6 | 0.4 | 2.5 |

As can be seen in Table 4, the yields of the target compound, Cl(CH$_2$)$_3$SiMe$_2$(OH$_2$CH$_3$), were not substantially increased by increasing the time of reaction from one hour to two hours. This indicates catalyst degradation.

Examples 17-20

The same procedure and reactant amounts as were used in examples 1-6 were used in examples 17-20 with the following differences: the reactants were heated to and held at 40° C.; the amount of catalyst was reduced to 10 mole ppm; the catalyst solvent was allyl chloride in all cases; and nitrogen was bubbled into the tubes of the examples according to the invention to deoxygenate the reactants and reaction atmosphere. The results, which are an average of two trials, are listed in Table 5,

TABLE 5

Comparison of the catalyst of the invention and a comparative catalyst at 10 mole ppm, 40° C. reaction temperature for one hour, and with nitrogen and air atmospheres.

| | | | Reaction Products and By-Products Yield (%) | | |
|---|---|---|---|---|---|
| Example No. | Catalyst | Atmosphere | A | B | C |
| 17 (comparative) | [Ir(COD)Cl]$_2$ | Air | 23.7 | 0.2 | 2.0 |
| 18 (comparative) | [Ir(COD)Cl]$_2$ | Nitrogen | 79.4 | 2.0 | 1.7 |
| 19 | Ir(acac)(COD) | Air | 10.4 | trace | 2.0 |
| 20 | Ir(acac)(COD) | Nitrogen | 64.7 | 0.4 | 1.7 |

As can be seen in Table 5, the yields of the target compound, Cl(CH$_2$)$_3$SiMe$_2$(OEt), were greatly increased when the reaction atmosphere was deoxygenated according to the process in examples 18 and 20 compared with comparative examples 17 and 19 which were conducted under an air atmosphere.

Examples 21-31

Iridium catalyst or other catalyst was dissolved in allyl chloride. The iridium and allyl chloride catalyst solution was then added to the glass tube of multi-tube batch reactor described for Example 1. After the any additional allyl chloride was added, the tube was cooled in dry ice to −78° C. Similarly cooled triethoxyhydridosilane was then added to the tube, and the reaction mixture was then heated to and held at the target temperature for the prescribed time. After the prescribed time, the reaction was stopped, or quenched, by again cooling with dry ice. The resulting mixture was analyzed by gas chromatography (GC) to determine the % of each of the major materials present. The reaction conditions and catalyst concentration for examples 21-31 are in Table 6 below. The results for the same examples are listed in Table 7,

TABLE 6

Reaction conditions and catalyst concentrations for Examples 21-31

| Example No. | Catalyst | Catalyst Conc. (mole ppm Ir) | Temp. (° C.) | Time (hrs.) | N$_2$ Purge |
|---|---|---|---|---|---|
| 21 (Comparative) | [Ir(COD)Cl]$_2$ | 208 | 60 | 1 | No |
| 22 (Comparative) | [Ir(COD)Cl]$_2$ | 715 | 60 | 1 | Yes |
| 23 (Comparative) | [Ir(COD)Cl]$_2$ | 476 | 40 | 1 | Yes |
| 24 (Comparative) | [Ir(COD)Cl]$_2$ | 100 | 40 | 2 | Yes |
| 25 (Comparative) | [Ir(COD)Cl]$_2$ | 1638 | 30 | 2 | Yes |
| 26 | Ir(acac)(COD) | 676 | 60 | 1 | Yes |
| 27 | Ir(acac)(COD) | 100 | 40 | 2 | Yes |
| 28 | Ir(acac)(COD) | 1252 | 30 | 2 | Yes |
| 29 (Comparative) | Platinum(4) | 241 | 60 | 1 | No |
| 30 (Comparative) | Pt(COD)Cl$_2$ | 321 | 60 | 1 | No |
| 31 (Comparative) | Pt(COD)Cl$_2$ | 1203 | 30 | 2 | No |

TABLE 7

Result of the hydrosilation reaction of Examples 21-28.

| Example No. | Reaction Products and By-Products Yield (%) | | | Selectivity+ (%) | Activity++ (%) |
|---|---|---|---|---|---|
| | D* | E* | F* | | |
| 21 (Comparative) | 48.4 | 24.8 | 4.2 | 62.5 | 94.0 |
| 22 (Comparative) | 34.8 | 33.2 | 5.7 | 47.2 | 93.3 |
| 23 (Comparative) | 43.9 | 7.7 | 2.4 | 81.2 | 59.3 |
| 24 (Comparative) | 21.8 | 2.1 | 1.3 | 86.5 | 29.0 |
| 25 (Comparative) | 48.8 | 16.2 | 2.9 | 71.9 | 77.8 |
| 26 | 31.6 | 34.4 | 5.6 | 44.2 | 91.7 |
| 27 | 15.2 | 1.2 | 0.9 | 87.5 | 19.2 |
| 28 | 47.4 | 23.5 | 3.3 | 63.8 | 90.5 |
| 29 (Comparative) | 14.2 | 27.8 | 21.2 | 22.5 | 81.0 |
| 30 (Comparative) | 11.8 | 27.4 | 19.3 | 20.2 | 92.4 |
| 31 (Comparative) | 8.2 | 21.0 | 15.5 | 18.3 | 62.0 |

+Selectivity is determined by dividing the yield of chloropropyltriethoxysilane by the sum of the yield of chloropropyltriethoxysilane, propyltriethoxysilane, and chlorotriethoxysilane and multiplying by one hundred.
++Activity is the sum of the yields of chloropropyltriethoxysilane, propyltriethoxysilane, and chlorotriethoxysilane.
*D represents chloropropyltriethoxysilane; E represents chlorotriethoxysilane; and F represents propyltriethoxylsilane.

Example 32

$[Ir(COD)(OCH_3)]_2$ (0.3 milligrams, 100 mole ppm iridium) was dissolved in 0.77 grams of allyl chloride and mixed at −78° C. in a tube of a multi-tube batch reactor described in example 1. Next, 1.06 grams of $CH_3HSi(OCH_3)_2$ were added to the tube, and the tube was heated at 80° C. for one hour. After one hour the tube was cooled with dry ice to quench the reaction. The crude reaction mixture was then analyzed by gas chromatography (GC) and the yield of chloropropylmethyldimethoxysilane was determined to be 47.5%.

Example 33

$[Ir(COD)(OCH_3)]_2$ (03 milligrams, 100 mole ppm iridium) was dissolved in 0.77 grams of allyl chloride and mixed at −78° C. in a tube of a multi-tube batch reactor described in example 1. Next, 1.22 grams of $HSi(OCH_3)_3$ were added to the tube, and the tube was heated at 80° C. for one hour. After one hour the tube was cooled with dry ice to quench the reaction. The crude reaction mixture was then analyzed by gas chromatography (GC) and the yield of chloropropyltrimethoxysilane was determined to be 42.7%.

That which is claimed is:

1. A process for preparing a haloalkylalkoxysilane, the process comprising:
reacting a silane of formula (II),

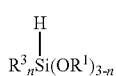
(II)

wherein each $R^1$ and $R^3$ are independently alkyl groups having from 1 to 6 carbon atoms and n has a value of 0, 1 or 2, with an alkenylhalide compound of formula (III),

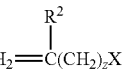
(III)

wherein $R^2$ is hydrogen or an alkyl group having from 1 to 6 carbon atoms; X is chloro, fluoro, bromo, or iodo; and z is an integer from 1 to 5, in the presence of a catalytic amount of and iridium containing catalyst having formula (V):

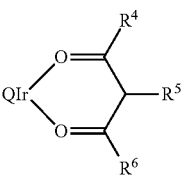
(V)

wherein Q is selected from 1,3-butadiene, 1,3-hexadiene, 1,3-cyclohexadiene, 1,3-cyclooctadiene, 1,5-cyclooctadiene and norbornadiene; $R^4$ is independently hydrocarbyl, halohydrocabyl, cyanoalkyl, alkoxy, cyanoalkoxy, amino, or hydrocarbyl-substituted amino; $R^5$ is independently hydrogen, hydrocarbyl, halohydrocarbyl, or acyl; and $R^6$ is independently hydrocarbyl, halohydrocarbyl, or cyanoalkyl, wherein the reacting is conducted under an atmosphere containing <5% (v/v) oxygen.

2. The process of claim 1 wherein the haloalkylalkoxysilane produced comprises a compound of formula (I)

(I)

wherein $R^1$, $R^2$, $R^3$, X, n, and z are as defined in claim 1.

3. The process of claim 1 wherein $R^3$ is independently methyl, ethyl, propyl, isopropyl or butyl.

4. The process of claim 1 wherein $R^1$ is independently methyl, ethyl, propyl, isopropyl, or butyl.

5. The process of claim 1 wherein $R^1$ is independently methyl or ethyl, n equals 0, X is chloro and $R^2$ is H.

6. The process of claim 1 wherein $R^3$ is methyl, $R^1$ is independently ethyl or methyl, n equals 1, X is chloro and $R^2$ is H.

7. The process of claim 1 wherein $R^3$ is methyl, $R^1$ is independently ethyl or methyl, n equals 2, X is chloro, and $R^8$ is H.

8. The process of claim 1 wherein the temperature is from 20° C. to 200° C.

9. The process of claim 1 wherein the silane or the alkenylhalide is a limiting reagent and the iridium catalyst is at 5 to 900 mole ppm of iridium based upon the limiting reagent.

10. A process for the preparation of a haloalkylhalosilane, the process comprising:
reacting a silane of formula (VI),

(VI)

wherein $R^3$ is an alkyl group having from 1 to 6 carbon atoms; X is chloro, bromo, fluoro, or iodo; and n has a value of 0, 1, or 2, with an alkenylhalide compound of formula (III),

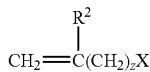
(III)

wherein $R^2$ is hydrogen or an alkyl group having from 1 to 6 carbon atoms; z is an integer from 1 to 5; and X is as defined above, in the presence of a catalytic amount of and iridium containing catalyst of formula (V),

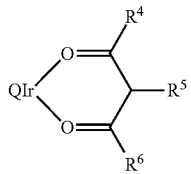
(V)

wherein Q is independently 1,3-butadiene, 1,3-hexadiene, 1,3-cyclohexadiene, 1,3-cyclooctadiene, 1,5-cyclooctadiene and norbornadiene; $R^4$ is independently hydrocarbyl, halohydrocabyl, cyanoalkyl, alkoxy, cyanoalkoxy, amino, or hydrocarbyl-substituted amino; $R^5$ is independently hydrogen, hydrocarbyl, halohydrocarbyl, or acyl; and $R^6$ is independently hydrocarbyl, halohydrocarbyl, or cyanoalkyl, and wherein the reacting is conducted under an atmosphere having an oxygen content below 5% (v/v).

11. The process of claim 10 wherein the haloalkylhalosilane produced comprises a compound of formula (IX),

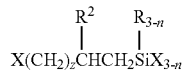
(IX)

wherein $R^2$, $R^3$, n, and z are as defined in claim 10 and each X is independently a chloro, bromo, fluoro, or iodo group.

12. The process of claim 11 further comprising reacting the haloalkylhalosilane produced with an alcohol containing 1 to 6 carbon atoms.

13. A process for increasing the activity of an iridium hydrosilation catalyst comprising reducing the oxygen content of a reaction atmosphere of a hydrosilation reaction mixture comprising a hydrosilation catalyst according to formula (V)

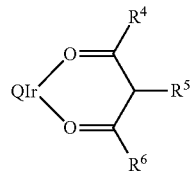
(V)

wherein Q is independently 1,3-butadiene, 1,3-hexadiene, 1,3-cyclohexadiene, 1,3-cyclooctadiene, 1,5-cyclooctadiene or norbornadiene; $R^4$ is independently hydrocarbyl, halohydrocabyl, cyanoalkyl, alkoxy, cyanoalkoxy, amino, or hydrocarbyl-substituted amino; $R^5$ is independently hydrogen, hydrocarbyl, halohydrocarbyl, or acyl; and $R^6$ is independently hydrocarbyl, halohydrocarbyl, or cyanoalkyl, to an oxygen content below 5% (v/v).

* * * * *